US00PP18985P2

(12) United States Plant Patent
Hanes

(10) Patent No.: US PP18,985 P2
(45) Date of Patent: Jun. 24, 2008

(54) ***VERBENA* PLANT NAMED 'LAN UPVIOT'**

(50) Latin Name: *Verbena hybrida*
Varietal Denomination: Lan Upviot

(75) Inventor: Mitchell E. Hanes, Morgan Hill, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 11/709,474

(22) Filed: Feb. 22, 2007

(51) Int. Cl.
*A01H 5/00* (2006.01)

(52) U.S. Cl. ..... Plt./308

(58) Field of Classification Search ..... Plt./308
See application file for complete search history.

*Primary Examiner*—Kent L. Bell
(74) *Attorney, Agent, or Firm*—Jondle & Associates, P.C.

(57) ABSTRACT

A *verbena* cultivar particularly distinguished by its violet colored flowers, vigorous, free-branching, upright growth habit, and tolerance to powdery mildew is disclosed.

2 Drawing Sheets

Genus and species: *Verbena hybrida*
Variety denomination: 'Lan Upviot'.

BACKGROUND OF THE NEW PLANT

The present invention comprises a new and distinct cultivar of *verbena,* botanically known as *Verbena hybrida,* and hereinafter referred to by the cultivar name 'Lan Upviot'. The new cultivar originated in 2003 in Gilroy, Calif. from the self-pollination of '1658-1', an unpatented blue flowered proprietary *verbena.*

The seeds produced by the self-pollination were sown in June 2003. A single plant selection was chosen for further evaluation and for asexual propagation in September 2003.

The new cultivar was created in 2003 in Gilroy, Calif. and has been asexually reproduced repeatedly by vegetative cuttings and tissue culture in Gilroy, Calif. and Andijk, The Netherlands over a three-year period. The plant has also been trialed at Gilroy, Calif., Andijk, The Netherlands and Hillscheid, Germany. The present invention has been found to retain its distinctive characteristics through successive asexual propagations.

Plant Breeder's Rights for this cultivar have been applied for in Switzerland on Oct. 30, 2006.

SUMMARY OF THE INVENTION

The following are the most outstanding and distinguishing characteristics of the new cultivar when grown under normal horticultural practices in Gilroy, Calif. and Andijk, The Netherlands.

1. Violet flowers;
2. Upright plant growth habit;
3. Vigorous and free branching; and
4. Tolerance to powdery mildew.

DESCRIPTION OF THE PHOTOGRAPHS

This new *verbena* plant is illustrated by the accompanying photographs which show overall plant habit, including blooms, buds and foliage of the plant. The photographs were taken in August 2006. The colors shown are as true as can be reasonably obtained by conventional photographic procedures.

DESCRIPTION OF THE NEW CULTIVAR

Figure 1:
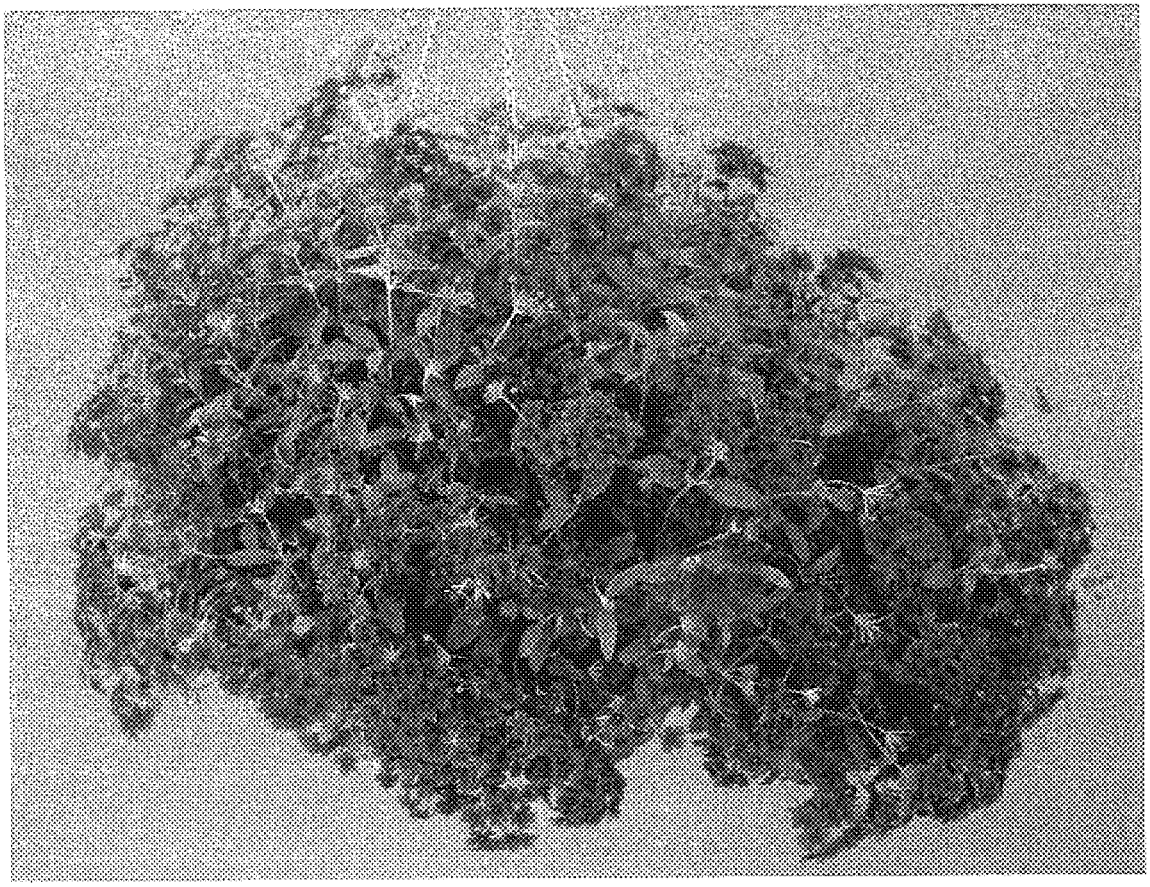
FIG. 1 shows the overall plant habit, including blooms, buds and foliage of plants approximately 18 to 22 weeks old in a hanging basket, in Andijk, The Netherlands.
Figure 2:
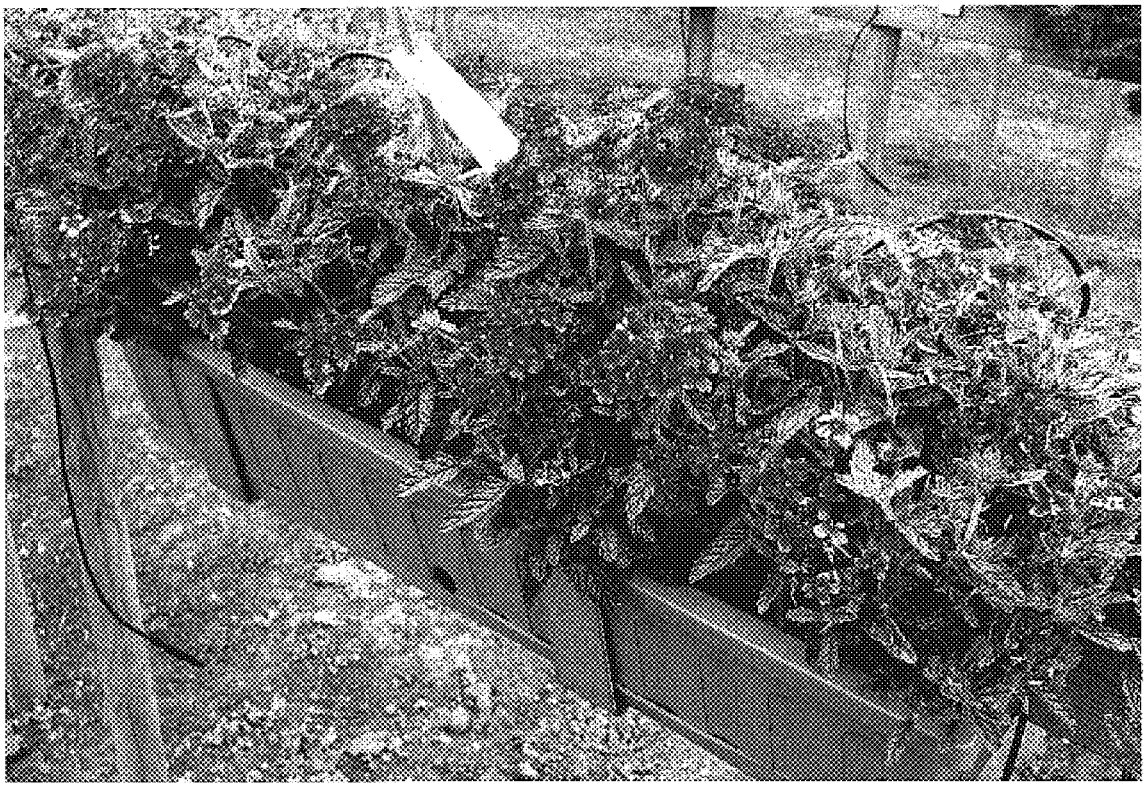
FIG. 2 shows the overall plant habit, including blooms buds and foliage of plants approximately 24 weeks old in Hillscheid, Germany.

The following detailed descriptions set forth the distinctive characteristics of 'Lan Upviot'. The data which define these characteristics were collected from asexual reproductions carried out in Gilroy, Calif. The plant history was taken from plants approximately 20 to 24 weeks old, grown in 6-inch pots in Gilroy, Calif. The plants had one plant growth regulator treatment and one terminal pinch after cuttings were transplanted form 4-inch pots to 6-inch pots. Color readings were taken in a LEXAN covered greenhouse in the summer under natural light. Color references are primarily to the R.H.S. Colour Chart of The Royal Horticultural Society of London (R.H.S.) (2001 edition). Texture description details were observed with a dissecting microscope.

DETAILED BOTANICAL DESCRIPTION

Classification:
*Botanical.—Verbena hybrida.*
*Common name.—Verbena.*

Parentage: Self-pollination of '1658-1' a proprietary *verbena* plant having blue flowers (unpatented).

Growth:
*Form.*—Herbaceous annual; mostly upright growth in the early stages though semi-compact, then becoming slightly spreading and decumbent plant habit.
*Growth and branching habit.*—Vigorous and free-branching with multiple secondary lateral branches.
*Height* (*measured from the top of the soil, including flowers*).—24.0 cm to 28.0 cm.
*Width* (*horizontal plant diameter*).—40.0 cm to 43.0 cm.

*Time to produce a finished flowering plant.*—Approximately 10 weeks for a 12-cm pot in the spring.

*Outdoor plant performance.*—Use in containers and hanging baskets.

*Time to initiate and develop roots.*—Approximately 7 to 10 days at 22 to 24 degrees Celsius.

*Root description.*—Fibrous, fleshy, white.

Leaves:

*Arrangement.*—Opposite.

*Immature leaf.*—Color: Upper surface: RHS 146A. Lower surface: RHS 147B.

*Mature leaf.*—Color: Upper surface: RHS 146A. Lower surface: RHS 147B. Length: 3.5 cm to 4.7 cm. Width: 1.7 cm to 2.3 cm. Shape: Lanceolate. Apex: Mucronulate. Base: Attenuate. Margin: Irregular, crenately incised. Texture: Upper surface: Hirsute, hispid and with a few translucent glandular hairs. Lower surface: Very pilose; many glandular hairs, all with a violet hue. Venation: Palmate. Venation color: RHS 144B.

*Petioles.*—Length: 0.7 cm to 1.0 cm. Diameter: 0.15 cm. Color: RHS 144B. Texture: Hirsute; pilose with a few glandular hairs, some with a violet hue.

Stems:

*Number of branches per plant.*—15 to 20.

*Color.*—RHS 145A.

*Length.*—15.0 cm to 20.0 cm.

*Diameter.*—0.2 cm.

*Internode length.*—1.7 cm to 2.0 cm.

*Texture.*—Hirsute; pilose with a few glandular hairs, some with a light violet hue.

*Stem anthocyanin.*—Absent.

Flower buds:

*Color* (*at tight bud*).—Between RHS 83B and RHS 83C.

*Shape.*—Tubular.

*Diameter.*—0.3 cm.

*Length.*—1.7 cm to 2.0 cm.

Inflorescence:

*Blooming habit.*—Flowers continuously from spring through fall; flowers appear about 9 to 10 weeks after planting of rooted cuttings.

*Lastingness of individual blooms on the plant.*—5 to 7 days.

*Fragrance.*—None.

*Inflorescence type.*—Terminal raceme.

*Horizontal diameter of inflorescence.*—5.4 cm to 5.7 cm.

*Vertical diameter of inflorescence.*—2.9 cm to 3.4 cm.

*Number of florets per raceme.*—13 to 19.

*Peduncle.*—Color: RHS 145B. Diameter: 0.15 cm. Length: 2.3 cm to 2.5 cm. Texture: Heavily pilose with glandular hairs, most with a violet hue.

Flowers:

*Floret form.*—Salverform; sessile on raceme.

*Floret diameter.*—1.9 cm to 2.1 cm.

*Number of petals and arrangement.*—Each floret is composed of 5 petals fused at the base.

*Immature flower.*—Color: Upper surface: Closest to RHS N81A with RHS 83A around the corolla opening. Lower surface: RHS N28B with RHS 83D at the margins.

*Mature flower.*—Color: Upper surface: Closes to RHS N81A with RHS 83A around the corolla opening. Lower surface: RHS N82B, with RHS 83D at the margins.

*Corolla.*—Color tube color (inside): RHS N155A. Tube length: 1.9 cm to 2.0 cm.

*Petals.*—Size: Length: 0.9 cm to 1.0 cm. Width: 0.7 cm to 0.8 cm. Lobe shape: Obovate. Apex: Emarginate. Base: Fused. Margin: Entire. Texture: Papillose.

*Calyx.*—General: Composed to five sepals fused to each other along their length, with a transparent membrane of less than 0.1 cm in width and with one smaller sepal (0.6 cm) attached to the base of the calyx. Color: RHS 143A for the outer surface; inner surface was not observed. Length: 1.0 cm to 1.1 cm. Width: 0.1 cm. Shape: Linear. Apex: Acute. Base: Fused. Margin: Entire. Texture: Hirsute; pilose with glandular hairs with a deep violet hue.

Reproductive organs:

*Stamens.*—Anthers and filaments are fused to the upper half of the corolla tube.

*Anther quantity.*—Four with two pollen sacs per anther.

*Anther length.*—0.1 cm.

*Pollen.*—Amount: Moderate. Color: RHS 1C.

*Pistil.*—1.

*Style length.*—2.0 cm to 2.1 cm.

*Style color.*—Closest to RHS N155B.

*Stigma color.*—RHS 144A.

Fruit/Seed set: Have not been observed.

Disease and insect resistance: Tolerance to powdery mildew.

COMPARISON WITH PARENTAL AND COMMERCIAL CULTIVARS

'Lan Upviot' differs from the proprietary, selfing parent '1658-1' (unpatented) in that 'Lan Upviot' has light violet flowers, while '1658-1' has blue flowers. Additionally, 'Lan Upviot' has a more compact and upright plant habit and darker green foliage than '1658-1'.

'Lan Upviot' differs from the commercial variety 'Balazlavi' (U.S. Plant Pat. No. 12,787) by having a smaller, more compact plant habit and larger and lighter colored leaves than 'Balazlavi'. Additionally, 'Lan Upviot' has darker violet flowers, while 'Balazlavi' has lavender flowers with white eyes.

I claim:

1. A new and distinct cultivar of *verbena* plant as shown and described herein.

* * * * *